(12) United States Patent
Cakmak

(10) Patent No.: US 11,052,253 B2
(45) Date of Patent: Jul. 6, 2021

(54) SYSTEM FOR DECREASING THE BLOOD PRESSURE

(71) Applicant: Yusuf Ozgur Cakmak, Avcilar/Istanbul (TR)

(72) Inventor: Yusuf Ozgur Cakmak, Avcilar/Istanbul (TR)

( * ) Notice: Subject to any disclaimer, the term of this patent is extended or adjusted under 35 U.S.C. 154(b) by 165 days.

(21) Appl. No.: 16/077,667

(22) PCT Filed: Feb. 24, 2016

(86) PCT No.: PCT/TR2016/000017
§ 371 (c)(1),
(2) Date: Aug. 13, 2018

(87) PCT Pub. No.: WO2017/146659
PCT Pub. Date: Aug. 31, 2017

(65) Prior Publication Data
US 2019/0070417 A1    Mar. 7, 2019

(51) Int. Cl.
| | |
|---|---|
| *A61N 1/36* | (2006.01) |
| *A61B 5/00* | (2006.01) |
| *A61B 5/021* | (2006.01) |
| *A61N 1/365* | (2006.01) |
| *A61N 1/04* | (2006.01) |

(52) U.S. Cl.
CPC .......... *A61N 1/36117* (2013.01); *A61B 5/021* (2013.01); *A61B 5/4836* (2013.01); *A61N 1/36014* (2013.01); *A61B 5/6824* (2013.01); *A61N 1/0456* (2013.01); *A61N 1/36564* (2013.01)

(58) Field of Classification Search
USPC ........................................................ 607/44
See application file for complete search history.

(56) References Cited

U.S. PATENT DOCUMENTS

| | | | |
|---|---|---|---|
| 2004/0220621 A1 | 11/2004 | Zhou et al. | |
| 2011/0301662 A1 | 12/2011 | Bar-Yoseph et al. | |
| 2013/0304169 A1 | 11/2013 | Simon | |
| 2015/0057313 A1* | 2/2015 | Joyner | A61N 1/3611 514/329 |
| 2015/0297139 A1* | 10/2015 | Toth | A61B 18/1492 600/381 |

FOREIGN PATENT DOCUMENTS

| | | |
|---|---|---|
| WO | 2008/143814 A2 | 11/2008 |
| WO | 2013/134121 A2 | 9/2013 |

OTHER PUBLICATIONS

International Search Report and Written Opinion for corresponding PCT application No. PCT/TR2016/000017, dated Nov. 22, 2016.
Second Written Opinion for corresponding PCT application No. PCT/TR2016/000017, dated Jan. 31, 2018.
International Preliminary Examination Report and Annexes for corresponding PCT application No. PCT/TR2016/000017, dated May 17, 2018.

* cited by examiner

*Primary Examiner* — Nicole F Lavert
(74) *Attorney, Agent, or Firm* — Notaro, Michalos & Zaccaria P.C.

(57) ABSTRACT

A blood pressure decreasing system that decreases blood pressure of a patient by noninvasively blocking the sympathetic innervation of the kidney, blocking all three pathways of the sympathetic nerves to adrenal gland medulla and expanding the renal artery of the patient. The blood pressure decreasing system has at least one sensor for measuring the blood pressure of the patient and generates systolic blood pressure value and/or diastolic blood pressure value; at least two electrodes that are placed to skin dermatomal of the patient; at least one stimulator that sends electrical signals to electrodes in order to block the sympathetic nerve innervation to arterial smooth muscle and kidney, all three pathways of the sympathetic nerves to adrenal medulla and expand renal artery of the patient; and at least one control unit, which receives the blood pressure values from said sensor, compares received values with predetermined threshold values and controls the stimulator.

24 Claims, No Drawings

SYSTEM FOR DECREASING THE BLOOD PRESSURE

FIELD OF INVENTION

The present invention relates to a system for decreasing blood pressure in order to treat hypertension.

PRIOR ART

Hypertension is a medical condition, in which blood pressure in the arteries is higher than optimal values. Blood pressure is measured by two parameters; systolic (maximum) pressure and diastolic (minimum) pressure. Optimal values for said parameters for and adult are 140 mmHg and 90 mmHg respectively. When systolic blood pressure of a person is above 140 mmHg, said person is usually considered having hypertension.

Although hypertension does not directly harm a patient, it causes other heart diseases (such as hypertensive heart disease and coronary artery disease), brain diseases (such as stroke) and artery diseases (such as aortic aneurysm and peripheral artery disease). Therefore, hypertension may cause dangerous medical conditions and treating hypertension has utmost importance to improve life expectancy of the patients.

In order to provide a treatment to hypertension, reasons for the high blood pressure should be examined. Researches show that, the high blood pressure is related to the kidneys and adrenal glands. In detail, if kidneys and adrenal gland are stimulated by sympathetic innervation blood filtration in kidney differs, blood pressure increasing hormones secreted and high blood pressure problem occurs. Therefore, in order to reduce blood pressure, sympathetic innervation to kidney and adrenal gland and those organs' arterial smooth muscles should be decreased or be blocked.

One solution for improving efficiency of the kidneys is using medications. Although medications reduces blood pressure some cases, because of the side effects of the medications, this treatment method is not preferred by some patients. Moreover, medications are usually unable to reduce blood pressure of the patients having renal artery stenosis.

Another solution for decreasing the blood pressure is to block sympathetic innervation to the kidneys and adrenal gland. This solution also results with expanding the kidney (renal) arteries because of the sympathetic denervation to smooth muscles of the renal arteries. Patent document WO2013134121A2 discloses a device for regulating the blood pressure and heart rate. According to this document, at least two electrodes are implanted to nerves and/or arteries of the patient. By sending electrical signals to the nerves and/or arteries of the patient through said electrodes, sympathetic nerves can be blocked on kidney (renal) arteries of the patient and as a consequence the dilatation of the renal arteries can be observed. However, according to this document, a medical surgery is required in order to implant said electrodes. In addition, adrenal gland contribution is not indicated as well as the blocking the sympathetic nerves on the renal arterial wall can not block total adrenal gland sympathetic innervation because of the adrenal gland's two other arterial blood supply which are not originated from the renal artery and includes sympathetic nerves.

BRIEF DESCRIPTION OF INVENTION

Present application discloses a blood pressure decreasing system that decreases blood pressure of a patient by blocking the sympathetic nerve innervation to kidney and all three paths of the sympathetics to adrenal gland medulla and the blockage of the sympathetics accompanied by expansion of the renal artery of the patient. Said blood pressure decreasing system comprises at least one sensor for measuring the blood pressure of said patient and generates systolic blood pressure value and/or diastolic blood pressure value; at least two electrodes that are placed to skin dermatomal of said patient; at least one stimulator that sends electrical signals to said electrodes in order to block the autonomic innervation but mostly the sympathetic nerve innervation to arterial smooth muscle of the renal artery and kidney, and adrenal gland and also expand renal artery; and at least one control unit, which receives the blood pressure values from said sensor, compares received values with predetermined threshold values and control said stimulator according to the result of said comparison.

According to the present application, since electrodes are placed above the dermatomes (in other words since electrodes are placed to the skin), blood pressure decreasing system is used by the patients easily. Moreover, according to the present application, nerves or arteries of the patient are not damaged and the system is non-invasive and temporary. Therefore, blood pressure of the patient is reduced easily and without causing any damage.

Object of Invention

Object of the present application is to provide a system for decreasing the blood pressure of a patient.

Another object of the present application is to provide a wearable system.

Another object of the present application is to provide a system that measures blood pressure of a patient and reduce the blood pressure of the patient if measured value is above a predetermined threshold value.

DETAILED DESCRIPTION OF INVENTION

Hypertension is a dangerous medical condition, which may cause heart diseases, brain diseases and artery diseases. One of the reasons of the hypertension is lack of blood filtering efficiency of the kidneys. Therefore, in the present application, a system for decreasing blood pressure in order to treat hypertension by non-invasively blocking the sympathetic innervation of the kidney, all three sympathetic paths to adrenal gland medulla and smooth muscles of the renal and suprarenal gland arteries.

Blood pressure decreasing system of the present application decreases blood pressure of a patient by non-invasively blockage of the sympathetic innervation to kidney, all three pathways of the sympathetic innervation to adrenal gland medulla in addition to smooth muscles of the renal artery which expands the renal artery. Said system comprises, at least one sensor for measuring the blood pressure of said patient and generates systolic (maximum) blood pressure value and/or diastolic (minimum) blood pressure value; at least two electrodes that are placed to skin dermatomal (a skin area that is supplied by a nerve) of said patient; at least one stimulator that sends electrical signals to said electrodes in order to block the sympathetic nerve innervation to arterial smooth muscle of the renal artery, kidney and all three pathways of the sympathetic branches to adrenal gland medulla, and also expand renal and suprarenal gland arteries of the patient; and at least one control unit, which receives the blood pressure values from said sensor, compares received values with predetermined threshold values and control said stimulator according to the result of said comparison. Said system may further comprise at least one power source (for example a rechargeable battery) for energizing the control unit and/or electrodes. In an alternative embodiment, blood pressure decreasing system comprises a power generator that generated electrical power from the body (skin) of the user for energizing the control unit and/or electrodes.

In a preferred embodiment of the present application, said signal has frequency 1-60 Hz (more preferably 10 Hz) or a burst frequency of 50-120 Hz with 1-10 Hz frequency. Current of the signal is preferably between 10-20 mA (more preferably 15 mA). Voltage of the signal is preferably between 1-15 V (more preferably 5 V). Duration of the signal is preferably between 0.1-300 μs (more preferably 100 μs).

In an exemplary embodiment of the present application, said electrodes are placed over the skin segments of T5-S2 (preferably T10, and/or T12 and/or L4 and/or L5) which includes sympathetic nerve fibers originating from the same spinal cord levels that the kidney and adrenal gland medulla are innervated. T5-S2 skin segments are used to stimulate related sympathetic nerves and said sensors are placed to wrist or upper arm of a patient. One of said electrodes are used as anode and other one is used as cathode. Then, blood pressure values measured by said sensors are sent to said control unit. In the control unit, systolic blood pressure value and/or diastolic blood pressure value are compared with the predetermined threshold values. For example, systolic blood pressure value is compared with 140 mmHg value and diastolic blood pressure value is compared with 90 mmHg value. If at least one of the measured values is higher than the related threshold value, control unit enables said stimulator to send electrical signals to the electrodes. When the nerves on said dermatome are excited with the specific signal, sympathetic innervation to renal arterial smooth muscle, kidney and adrenal gland itself is blocked (so that the neuronal communication of the kidney and adrenal gland and autonomic nerve system will be blocked and as a consequence there wont be influences of the central sympathetic outflow to kidney and adrenal gland or kidney's feedback to central autonomic nerve system to increase blood pressure with neuroendocrine response). In other words, said signal with specific frequency blocks the neural connection between the autonomic nerve system and kidney, and adrenal gland. Moreover, thanks to said signal, renal artery of the patient is expanded as well. Studies show that, said signal also blocks neural connection between the autonomic nerve system and adrenal gland. When this neural connection is blocked with the signal having specific frequency, kidney and adrenal gland no more releases hormones that increase the blood pressure.

Sympathetic stimulation to kidney results with the increased renin secretion, decreased urinary sodium excretion and decreased renal flow. Those cascades results with increased blood pressure. Sympathetic innervation to medulla of the adrenal gland results with the secretion of adrenalin and noradrenaline to blood which increased blood pressure. Blockage of adrenal gland medulla's sympathetic innervation can also overcome adrenalin and noradrenalin contribution to mechanism that increase blood pressure. Therefore, in order to reduce blood pressure, blockage of sympathetic innervation to kidney and adrenal gland is necessary. Additionally the segmental skin stimulation not only act over the sympathetic nerves over the renal artery that gives inferior suprarenal artery branch to adrenal medulla and carries sympathetic innervation to adrenal medulla, but also the small portion of sympathetic nerves that reach to the adrenal medulla with alternative pathways like using the superior and middle suprarenal arteries as a path. The segmental skin stimulation also blocks the rare sympathetic nerves over the suprarenal and middle renal artery through related segmental skin stimulation so that the stimulation acts on the main sympathetic nerves reaching to the adrenal medulla with the aid of infrerior suprarenal artery (a branch of renal artery), but also the alternative paths of the sympathetic nerves to adrenal medulla with the aid of middle renal artery (a branch of abdominal aorta), and superior suprarenal artery (a branch of inferior phrenic artery).

A second additional approach can be parasympathetic nerve stimulation approach however there is no to little contribution of parasympathetic innervation to kidney from vagus and sacral S2, S3, S4 levels so that additional or sole stimulation of those regions may also contribute lowering the blood pressure by their central effects mostly.

Vagal component of the parasympathatic nerve system to decrease blood pressure has its cutaneous branches only in the ear skin, specifically concha area and external auditory canal. The vagus nerve can directly stimulated from the ear skin area as well as with indirect way of stimulations like: median and common peroneal nerve stimulation, decreasing breath rate and ocular compression.

Therefore, in another preferred embodiment of the present application, blood pressure level decreasing system comprises at least two additional electrodes that are placed the ear skin, median nerve and peroneal nerve territories in addition to guided systems to decrease breathing rate and ocular compression in order to stimulate the parasympathetic nerve system (vagus nerve) to liver. Frequency of the signal sent to said additional electrodes is 1-100 Hz (more preferably 2-10 Hz) or a burst frequency of 50-120 Hz with 1-10 Hz frequency.

In another preferred embodiment of the present application, frequency, voltage, current and/or duration of said signal depends on the result of said comparison. For example, if systolic blood pressure value is higher than 140 mmHg and diastolic blood pressure value is less than 90 mmHg, optimum value of the frequency is 10 Hz, optimum value of the current is 12 mA, optimum value of the voltage is 5.5 V and optimum value of the signal duration is 120 μs. Wherein, if systolic blood pressure value is higher than 140 mmHg and diastolic blood pressure value is higher than 90 mmHg, optimum value of the frequency is 10 Hz with 80 Hz burst frequency, optimum value of the current is 12 mA, optimum value of the voltage is 5.5 V and optimum value of the signal duration is 140 μs. If systolic blood pressure value is less than 140 mmHg and diastolic blood pressure value is higher than 90 mmHg, optimum value of the frequency is 2 Hz with 80-100 Hz burst frequency, optimum value of the current is 10 mA, optimum value of the voltage is 5 V and optimum value of the signal duration is 120 μs.

In another preferred embodiment of the present application, blood pressure decreasing system comprises one set of electrodes (for example an electrode pair) that are placed over the L4 and/or L5 dermatomes and another set of electrodes (for example an electrode pair) that are placed over the T10 and/or T12 dermatomes. In this embodiment, signals sent to different set of electrodes are able to be controlled separately (for example frequency and or voltage level of the electrodes placed over the L4 and/or L5 dermatomes can be different from the frequency and or voltage level of the electrodes placed over the T10 and/or T12 dermatomes). By controlling said set of electrodes separately, blood pressure reduction effect of the system is boosted.

In another preferred embodiment of the present application, blood pressure decreasing system comprises at least one screen. Said screen informs user about blood pressure values that measured by said sensor and/or operation status of the stimulator (for example signal parameters).

Optimum signal parameters for reducing the blood pressure may vary for different individuals. Said parameters may depend on age, weight, height and gender of the patient. Therefore, in another preferred embodiment of the present application, blood pressure decreasing system comprises at least one input means (for example a keyboard or a touchscreen) to control signal parameters. In an exemplary embodiment, users are able to enter their age, weight, height, and gender information through said input means. In another exemplary embodiment, users directly changes optimum signal parameters manually. In order to change said parameters manually, optimum parameters for one individual may be found by a physician prior to use of the blood pressure decreasing system.

In another preferred embodiment of the present application, said control unit comprises means for monitoring the current level of the signal that are sent to said electrodes. In this embodiment, if the current level drops below a predetermined level, control unit increases the voltage of the signal in order to increase the current level above said predetermined level. Therefore, it is ensured that current level of the signal is high enough to block the autonomic innervation. In alternative embodiments, said control unit may comprise means for monitoring the frequency and/or wavelength (duration) of the signal. Therefore, it is ensured that signal parameters are correct.

In another embodiment, control unit comprises at least one short circuit control element. In this embodiment, if a short circuit situation occurs (for example because of misplacing the electrodes); signal sent to the electrodes is cut. Therefore, damaging the electrodes or control unit is prevented.

In another embodiment of the present application, blood pressure decreasing system of the present application comprises at least one remote control unit and at least one transmitter, which receives commands from said remote control and control the control unit according to the received commands. In this embodiment, by using remote control unit, said signal could be sent to the electrodes manually even if blood pressure of a patient is not higher than said predetermined threshold value. Therefore, it is prevented that blood pressure of a patient increases above a dangerous level during a critical operation (for example during a surgery).

In another preferred embodiment of the present application, control unit comprises at least one open circuit control element. In this embodiment, if electrical connection between electrodes is cut (for example because of damaging at least one electrode) users are able to be notified. In order to notify the user, blood pressure decreasing system comprises at least one alarming unit (for example a buzzer or a warning light).

In another preferred embodiment of the present application, each of said electrodes comprises an anode or a cathode connection and a pair of anode and cathode connection. In this embodiment, said electrodes are called intelligent electrodes. During the normal use of the blood pressure decreasing system, anode connection of one electrode and cathode connection of other electrode is used for transmitting signals to the dermatomes. If any open circuit situation occurs, for example if one of the electrodes is damaged, signal is transmitted to the dermatomes through pair of anode and cathode connection of other electrode.

In another preferred embodiment of the present application, blood pressure decreasing system comprises at least one temperature sensor, which measures the temperature of the electrodes and skin of the user, and at least one temperature adjusting unit, which adjusts the temperature of the electrode according to the temperature values measured by said temperature sensor. In this embodiment, if temperature of the electrode is higher than the temperature of the skin of the user, said temperature adjusting unit decreases the temperature of the electrode. Similarly, if temperature of the electrode is lower than the temperature of the skin of the user, said temperature adjusting unit increases the temperature of the electrodes. Therefore, it is ensured that said electrodes do not damage the skin of the user because of a high or low temperature.

According to the present application, since electrodes are placed above the dermatomes (in other words since electrodes are placed to the skin), blood pressure decreasing system is used by the patients easily. Moreover, according to the present application, nerves or arteries of the patient are not damaged and the system is non-invasive and temporary. Therefore, blood pressure of the patient is reduced easily and without causing any damage.

The invention claimed is:

1. A blood pressure decreasing system for decreasing blood pressure of a patient by blocking the sympathetic nerves to kidney and all three sympathetic pathways to adrenal gland medulla accompanied by expansion of the renal artery of the patient, characterized by comprising;
   at least one sensor for measuring the blood pressure of said patient and generating systolic blood pressure value and/or diastolic blood pressure value;
   one set of electrodes that are adapted to be placed over L4 and L5 dermatomes and another set of electrodes that are adapted to be placed over T10 and T12 dermatomes of said patient;
   at least one stimulator for sending electrical signals to said electrodes for blocking the sympathetic nerve innervation to arterial smooth muscle of the renal artery, kidney and all three pathways of the sympathetic branches to adrenal gland medulla, said at least one stimulator for sending electrical signals to said electrodes also for expanding renal and suprarenal gland arteries of the patient, whereby the at least one stimulator is effective to decrease blood pressure of the patient; and
   at least one control unit for receiving predetermined threshold values, for receiving the blood pressure values from said sensor, and for comparing the blood pressure values received from the sensor with the predetermined threshold values and controlling said stimulator according to the result of said comparison.

2. A blood pressure decreasing system according to claim 1, characterized in that; said signal has frequency 1-60 Hz.

3. A blood pressure decreasing system according to claim 2, characterized in that; said signal has frequency 10 Hz.

4. A blood pressure decreasing system according to claim 1, characterized in that; said signal has frequency has a burst frequency of 50-120 Hz with 1-10 Hz frequency.

5. A blood pressure decreasing system according to claim 1, characterized in that; current of the said signal is between 10-20 mA.

6. A blood pressure decreasing system according to claim 1, characterized in that; current of the said signal is 15 mA.

7. A blood pressure decreasing system according to claim 1, characterized in that; voltage of said signal is between 1-15 V.

8. A blood pressure decreasing system according to claim 1, characterized in that; voltage of said signal is 5 V.

9. A blood pressure decreasing system according to claim 1, characterized in that; duration of said signal is between 0.1-300 µs.

10. A blood pressure decreasing system according to claim 1, characterized in that; duration of said signal is 100 µs.

11. A blood pressure decreasing system according to claim 1, characterized by further comprising; further comprise at least one power source for energizing the control unit and/or electrodes.

12. A blood pressure decreasing system according to claim 1, characterized by further comprising; at least one power generator that generated electrical power from the body of the user for energizing the control unit and/or electrodes.

13. A blood pressure decreasing system according to claim 1, characterized by further comprising; at least one screen.

14. A blood pressure decreasing system according to claim 1, characterized by further comprising; at least one input means.

15. A blood pressure decreasing system according to claim 1, characterized in that; said control unit comprises means for monitoring the current level of the signal that are sent to said electrodes.

16. A blood pressure decreasing system according to claim 1, characterized in that; control unit comprises at least one short circuit control element.

17. A blood pressure decreasing system according to claim 1, characterized by further comprising; at least one remote control unit and at least one transmitter, which receives commands from said remote control and control the control unit according to the received commands.

18. A blood pressure decreasing system according to claim 1, characterized in that; control unit comprises means for monitoring the frequency of the signal.

19. A blood pressure decreasing system according to claim 1, characterized in that; control unit comprises means for monitoring the wavelength of the signal.

20. A blood pressure decreasing system according to claim 1, characterized in that; control unit comprises at least one open circuit control element.

21. A blood pressure decreasing system according to claim 20, characterized by further comprising; at least one alarming unit.

22. A blood pressure decreasing system according to claim 1, characterized in that; each of said electrodes comprises an anode or a cathode connection and a pair of anode and cathode connection.

23. A blood pressure decreasing system according to claim 1, characterized by further comprising; at least one temperature sensor, which measures the temperature of the electrodes and skin of the user, and at least one temperature adjusting unit, which adjusts the temperature of the electrode according to the temperature values measured by said temperature sensor.

24. A blood pressure decreasing system according to claim 1, characterized by further comprising; at least two additional electrodes that are adapted to be placed on the ear skin.

* * * * *